United States Patent [19]

Fuhrmann

[11] Patent Number: 5,476,637
[45] Date of Patent: Dec. 19, 1995

[54] METHOD AND DEVICE FOR THE, MEASUREMENT OF IMPURITIES IN A LIQUID MORE PARTICULARLY WATER

[75] Inventor: Hans Fuhrmann, deceased, late of Hamburg, Germany, by Gertrud Fuhrmann, heir

[73] Assignee: Hans-Dieter Schultz, Hamburg, Germany

[21] Appl. No.: 147,101

[22] Filed: Nov. 1, 1993

Related U.S. Application Data

[63] Continuation of Ser. No. 865,922, Apr. 9, 1992, abandoned.

[51] Int. Cl.[6] .................................................. G01N 25/00
[52] U.S. Cl. ........................... 422/68.1; 73/19.1; 73/64.56
[58] Field of Search ............................ 422/68.1, 78, 79, 422/80; 436/62, 175, 177, 158, 143; 73/19, 61.41, 61.43, 61.55, 61.56, 64.56

[56] References Cited

U.S. PATENT DOCUMENTS

| | | | |
|---|---|---|---|
| 3,205,045 | 9/1965 | Von Lossberg | 422/79 |
| 3,322,504 | 5/1967 | Capuano | 422/79 |
| 3,607,076 | 9/1971 | Paine | 436/158 X |
| 3,826,618 | 7/1974 | Capuano | 422/78 |
| 3,849,070 | 11/1974 | Garza et al. | 436/133 |
| 3,854,881 | 12/1974 | Cohen | 422/79 |
| 3,922,904 | 12/1975 | Williams et al. | 73/19.1 |
| 3,929,003 | 12/1975 | Llewellyn | 73/61.72 |
| 4,063,446 | 12/1977 | Fuhrmann | 73/1 G |
| 4,129,179 | 12/1978 | Molitor | 165/101 |
| 4,198,208 | 4/1980 | Lerner et al. | 422/78 |
| 4,230,665 | 10/1980 | Huber | 422/64 |
| 4,248,598 | 2/1981 | Blunck | 422/78 |
| 4,288,229 | 9/1981 | Mar | 422/79 |
| 4,341,107 | 7/1982 | Blair et al. | 73/3 |
| 4,468,948 | 9/1984 | Nakayama | 73/19.1 |
| 4,783,343 | 11/1988 | Sato | 427/8 |
| 4,795,614 | 1/1989 | Norem et al. | 422/78 |
| 5,132,094 | 7/1992 | Godec et al. | 422/78 |
| 5,160,064 | 11/1992 | Nakamura et al. | 422/79 X |

OTHER PUBLICATIONS

S. Zumdahl. *Chemistry*, pp. 412–416, 1986.

*Primary Examiner*—Robert J. Warden
*Assistant Examiner*—Robert Carpenter
*Attorney, Agent, or Firm*—Anderson Kill Olick & Oshinsky

[57] ABSTRACT

A device for measuring of impurities in a liquid, especially water, consists of a mixing chamber 16 where the liquid is mixed with a carrier gas, wherein the impurities at least in part are transposed into the gaseous phase, a separation chamber 28 and a gas pick-up 34 for measuring the gas mixture generated during the mixing and composed of the carrier gas and the impurities, which were transposed into the gaseous phase, whereby an acquisition of all ever so slight impurity concentrations are possible with a comparatively simple construction.

4 Claims, 7 Drawing Sheets

METHOD AND DEVICE FOR THE MEASUREMENT OF IMPURITIES IN A LIQUID MORE PARTICULARLY WATER

This is a continuation application of Ser. No. 07/865,922, filed Apr. 9, 1992, now abandoned.

The present invention relates to a device for measuring impurities in a liquid, more particularly water, as well as to a method for this.

Owing to the increasing pollution of rivers and waters by foreign substances, in particular hydrocarbons and halogenated hydrocarbons, a measurement of ecologically harmful substances is urgently necessary. This also applies to the monitoring of communal and industrial effluents.

As a rule, the pollutions to be detected are of an organic nature, to be more specific, predominantly hydrocarbons dissolved in the water, halogenated hydrocarbons as well as toxic decomposition products based on the pollutions stated.

A continuous measurement is of advantage here so that a constant monitoring is provided and, on the one hand, also very short-term pollutions are reliably detected and, on the other, it is in each case possible to react very expeditiously subsequent to the occurrence of a pollution.

In such a monitoring, problems are caused also by the circumstance that very slight organic pollutants within the ppb and ppm range have to be reliably detected, which make exacting demands on the measuring technique.

Measurement methods are already know in which the measurement is performed by means of the absorption and desorption of the samples with the aid of special filter material and subsequent photometric or potentiometric evaluation. However, this unfortunately calls for manual interventions and can only be carried out discontinuously. By way of alternative, gas chromatographs are also employed in part which possess a hight degree of sensitivity and selectivity. However, it is true that gas chromatography does not permit a continuous monitoring of a liquid either. Moreover, the servicing costs are very high here as well, especially also on account of an auxiliary gas (hydrogen) being employed.

BACKGROUND OF THE INVENTION

A device for the continuous measurement of organic solvents in a liquid is known from the DE 31 26 648 C2. There, a semiconductor gas sensor is immersed into the liquid direct which, however, is separated from the liquid by means of a medium that is impervious to liquid. The liquid-impervious medium permits a diffusion of the dissolved free gases from the liquid to the semiconductor gas sensor so that the output signal of the latter is representative of the proportion of organic solvents in the liquid. But this device requires a direct immersion of the gas sensor into the liquid involving pertinent sealing problems. Besides, in the event of fluctuating liquid levels, a positional adjustment of the sensor may become necessary in order to ensure that the same is constantly immersed in the liquid but without being totally submerged in the latter. Moreover, the demands made with regard to the medium which is impervious to liquid and permits the gas to pass through are relatively high.

It is known furthermore from the DE 32 21 063 C3, to monitor a liquid by the addition of reagents for producing a chemical color reaction while use is made of a photometric measuring means. There, the reaction vessel is constructed in the form of a vertically disposed cylinder, into the underside of which the liquid to be monitored is introduced. In addition, supply lines terminate in the reaction vessel, via which it is possible to introduce various reagents in a controlled fashion.

The known apparatus requires somewhat more substantial constructional resources and exact dosing. Moreover, the flow of liquid has to be interrupted during a respective measurement so that no continuous monitoring of a liquid is possible.

The present invention is based upon the technical problem of providing a device and a method for the measurement of impurities in a liquid, more particularly water, which renders possible a detection of even very low impurity concentrations with a relatively simple construction.

SUMMARY OF THE INVENTION:

The present invention solves the technical problem discussed above by providing a device for the measurement of impurities in a liquid, more particularly in water and including a mixing chamber, in which the liquid is intermixed with a carrier gas, and as a result, the impurities are, at least in part, converted into gas phase and are measured by a gas sensor for the measurement of the gas mixture, which is formed by the intermixing and is composed of the carrier gas and the impurities converted into the gas phase.

In the invention, the liquid is thus intermixed with a carrier gas so that the impurities dissolved in the liquid are converted, at least in part, into the gas phase. The gas mixture comprised of the carrier gas and the impurity gases is measured with the aid of a gas sensor. Consequently, the gas sensor must not be brought into direct contact with the liquid so that no expensive shielding of the sensor from the liquid is necessary. This simplifies the construction. The intermixing of the liquid with the carrier gas may be effected continuously with the liquid in flow so that a continuous monitoring of the liquid can be achieved. It is also possible, of course, to perform the measurement discontinuously when, by way of example, merely random samples are desired or the flow of liquid only takes place in a discontinuous manner, as is the case with some effluents.

The intermixing of the liquid with the carrier gas can be carried out by simply introducing the carrier gas into the flow path of the liquid so that the apparatus-related costs are very low.

Preferably a separating chamber adjoins the mixing chamber in which the liquid is separated from the gas mixture. It is possible to effect this separation in an extremely simple manner in that the separating chamber has a greater vertical extension so that the liquid accumulates within the lower area, while the mixture of gas rises upwardly. In this case the mixing chamber may be constructed in the form of a narrow pipe which allows a highly effective intermixing of liquid and carrier gas to take place. Thereby the dissolved impurity gases are able to effectively pass over into the carrier gas so that comparatively high foreign gas concentrations are achieved in the carrier gas which can be reliably detected and evaluated.

In a preferred construction the gas sensor is disposed within the upper area of the separating chamber so that a wetting by liquid is avoided and the gas mixture to be measured flows automatically to the gas sensor.

For leading the liquid away, the separating chamber is preferably provided with an outlet. It is possible to drain off the liquid intermittently, in a continuous monitoring operation, however, it is by preference led away continuously so that the respective volume of liquid in the separating chamber and, thereby, also the volume of gas remain substantially constant and the gas measurement can consequently be effected precisely at a constant gas volume and pressure.

In a preferred construction, an overflow cap is provided inside the outlet which serves as a flexible closure so as to enable the liquid to run off continuously, but so that no gas is capable of escaping via the outlet. The gas mixture is therefore capable of escaping through apertures provided within the sensor area while flowing past the gas sensor. This permits an accurate measurement to take place.

It is advantageous to provide a heating means within the area of the mixing chamber so as to make it possible to maintain the temperature in the mixing chamber essentially constant. It is possible to thereby standardize the gas pressure in the mixing chamber and thus the rate of conversion of the dissolved impurities, more particularly the organic solvents, into the gas phase so that a respective impurity concentration results in a clear measured value of the gas sensor which is unaffected by the temperature. This ensures a high degree of measurement precision.

The heating means may be disposed on the outside of the mixing chamber or in the mixing chamber wall. By preference, however, it is mounted in the interior of the mixing chamber and is in direct contact with the liquid so that an immediate, effective and rapid thermal transmission to the liquid is guaranteed. This permits a speedy temperature adjustment. In addition, heating losses due to thermal radiation to the outside and the like are exceedingly low. It is consequently possible for the heating means to possess relatively small dimensions.

In order to detect the temperature of the liquid, in a preferred construction, a temperature detector is provided. The temperature signal of the temperature detector may be employed for the temperature regulation of the temperature of the liquid and/or as a correction signal for allocating the measurement signal emitted by the gas sensor to a specific impurity concentration in dependence of the characteristic diagram of the temperature.

For a calibration it is of advantage to conduct the carrier gas which preferably consists of solvent-free air, to the gas sensor direct. When measurement is carried out in this state, it is ensured that no impurity concentration, or merely negligibly low impurity concentrations are present in the gas so that the sensor measures pure carrier gas and its output signal can be calibrated as zero value.

In a preferred construction, a valve is provided in the carrier gas supply line, through which the carrier gas can be switched over either to the bypass line, to the gas sensor or to a pipe leading to the mixing chamber. It is possible in this connection to initiate the calibration operation by means of a single valve switchover to the bypass line.

In order to increase the accuracy of the calibration operation still further, the same may be performed with a standard solution. In order to make this possible, a valve is disposed preferably in the liquid supply line which can be switched over to the delivery of the standard solution to the mixing chamber. The normal flow of liquid is thus blocked and substituted by the standard solution. Consequently, precisely defined conditions exist during the calibration.

Any gas may be employed as a carrier gas provided that it is ensured that it is free from the impurities to be measured. In a particularly simple and effective construction, air is used as carrier gas which is aspirated via a filter, preferably an activated charcoal filter. With this, no carrier gas supply of its own is necessary which fits in with the simplicity and sturdiness and the non-stationary nature of the measurement device according to the invention.

It is possible to increase the measuring precision still further by the introduction of both the carrier gas as well as the liquid at a specific fixed ratio into the mixing chamber. This is preferably done by the synchronous operation of pumps which deliver the carrier gas and the liquid. From a control-technical point of view, it is especially simple to couple the pumps mechanically to each other.

The measuring accuracy can be increased still further when the gas sensor is provided with a heating means. It is possible to thereby set defined temperature conditions within the area of the gas sensor so that its measurement signal is not distorted by temperature drift effects or the like. By preference, the temperature is regulated in such a way that it lies above the temperature of the gas mixture to be measured. It can be avoided hereby that the gas mixture condenses within the area of the gas sensor and distorts the results of the measurement.

In a preferred construction, the mixing chamber is constructed in the form of an elongated, substantially horizontally proceeding pipe. The effective intermixing of the liquid with the carrier gas is achieved hereby so that the dissolved impurity gas present in the liquid is capable of diffusing over into the carrier gas, i.e. into the gas phase. The length of the pipe may e.g. be 100 mm with an internal diameter of 3 mm. The device according to the invention and the method according to the invention permit a reliable and precise measurement of impurities at relatively low costs. It is possible to monitor as impurities all those substances which it is possible to convert into the gas phase when intermixing the liquid with carrier gas. But in particular the invention also renders possible a stable as well as continuous monitoring of organic solvents in water, it being possible to use air as a carrier gas in a very simple manner. The invention permits the detection of even extremely low concentrations within the ppb or ppm range.

In an advantageous further construction of the invention, the carrier gas is introduced into the bottom area of the reaction chamber so that the gas bubbles forming in the liquid rise upwardly, as a result of which, on the one hand, a good intermixing effect is produced and, on the other, the impurities dissolved in the liquid, particularly gaseous impurities, are capable of effectively diffusing into the carrier gas bubbles. Fine-pore frit is advantageously disposed within the bottom area of the reaction chamber. The frit brings about a close contact of the carrier gas bubbles with the sample liquid so that an effective transition of the dissolved impurities into the carrier gas and, consequently, a very extensive degasification of the liquid is achieved. Moreover, the period of contact between carrier gas and liquid is extended altogether on account of the frit so that the quantitative effect of the conversion of the dissolved impurities into the gas phase is improved.

It is of advantage to dispsoe the liquid outlet within the lower area of the reaction chamber so that it is ensured that solely that liquid is drained off which has passed through the reaction chamber and consequently has released, at least in part, the impurities to be measured.

In order to ensure a certain liquid level in the reaction chamber at all times, the outlet pipe is preferably provided with an upwardly directed elbow. The reaction chamber consequently is incapable of inadvertently running dry. In addition, the liquid present at each time in the elbow acts as a gas seal so that the impurities converted into the gas phase cannot escape via the outlet, which would lead to measurement distortions.

By positioning the elbow in such a way that its maximum vertical extension lies below the roof area of the reaction chamber, it is automatically achieved that, when the outlet is open, each time a liquid level appears automatically in the reaction chamber which is determined by the height of the elbow. Thereby, abobe the liquid level, sufficient gas space remains in the reaction chamber, so that the gas mixture resulting from the carrier gas mixture and the impurity gases can be measured in the simplest construction direct within the roof area of the reaction chamber. But it is also possible to provide the gas sensor not within the reaction chamber roof area direct, but to let a measuring line issue from the same which leads to the gas sensor. Due to the spatial decoupling between reaction chamber and gas sensor achieved hereby, the freedom of constructiona layout is increased. In addition, the environmental conditions of the gas sensor with regard to temperature, moisture and the like can then be specifically defined independently of those of the reaction chamber.

The measuring line is preferably provided with a pipe heating means so that the temperature of the measuring gas is adjustable to defined values and/or a condensation of the measuring gas on the measuring line wall can be prevented.

In a preferred construction, the gas sensor is also accommodated in a heated sensor housing so that its temperature is adjustable to desired values. It is possible to thereby eliminate changes in the measuring signal caused by temperature with the same impurity concentration. In addition, also within the area of the gas sensor, no condensation phenomena take place.

In order to maintain the vapor pressure in the reaction chamber essentially constant, the reaction chamber is preferably maintained at a constant temperature. It is ensured hereby that the transition rate of the impurities into the gas phase is substantially and exclusively determined by the respective impurity concentration so that it is possible to achieve clear and meaningful measurement results.

The tempering of the reaction chamber can be ensured in a simple manner by it being disposed inside a temperature-controlled housing. By means of said housing it is also possible to ward off other environmental influences which could distort the measurements.

An overflow receptacle is preferably provided through which the liquid flows. Consequently, in the overflow receptacle, an essentially constant liquid supply volume is always present, from which the liquid can be removed and conducted to the reaction chamber. In order to be able to automatically report a running dry of the overflow receptacle, a float switch is preferably disposed in the overflow receptacle which, when the liquid level falls below a lower boundary value, generates an alarm signal.

The delivery of the liquid from the overflow receptacle to the reaction chamber is preferably effected with the aid of a hose-pipe with pump so that it is possible to regulate the delivery volume with the aid of the pump.

The precision and reproduceability of the measurement results can be increased still further by the liquid and the carrier gas being conveyed to the reaction chamber at a predetermined mutual delivery ratio. It is possible to set the deliveries here in each case to constant values. But even when variable deliveries are involved, e.g. because of different quantities of liquids, it is nonetheless ensured that the mixing ratio always is constant so that also the transition rate of the impurities into the carrier gas remains constant. With this the measurement result becomes essentially independent of the respective delivery.

In a preferred construction, air that is aspirated via a filter is employed as carrier gas. For this reason, no special carrier gas supply is required for the device according to the invention, which is conducive to the simplicity and sturdiness of the construction. Moreover, the device according to the invention can be universally employed everywhere where liquid has to be monitored for impurities.

In order to also be able to measure relatively warm liquids, an additional cooling means may be provided, with the aid of which the liquid is cooled prior to its introduction into the reaction chamber. It is possible to thereby adjust the liquid to defined temperature values so that reproduceable measurement results are obtained.

The invention permits a very simple but nevertheless effective measurement of impurities, such as e.g. organic pollutions, in which predominantly hydrocarbons dissolved in water, halogenated hydrocarbons or toxic decomposition products based on such pollutions are involved. On this occasion, the component to be measured, such as e.g. perchloroethylene or trichloroethylene, methylene chloride and others, as well as non-halogenated hydrocarbons, is converted into the gas phase. In this case, solvent-free air is used as carrier gas. The invention also permits the detection of extremely low concentrations within the ppb and ppm range. The operating method of the device according to the invention can be classified as a phase exchange method.

The trace measurement of the impurities converted into the gas phase is in this case advantageously performed on a physical basis with the aid of the gas sensor.

The invention is particularly well-suited in practical operation within the context of the environmental protection and permits a continuous measurement of certain group and sum parameters of impurities, especially organic solvents, in water. By way of example, it is thus possible, for the preparation of drinking water from bank-filtered water, to recognize in time short-term or long-term impurities in the raw water, e.g. in the event of an organic pollution of the river water, and to take appropriate steps. Also in the case of industrial accidents, e.g. in tank leakages, overflowing of tank trucks or tank cars and seepage of the noxious substances into the ground, it is possible to notice in time a possible spreading into the subterranean water. This applies to both mobile as well as stationary installations, e.g. in groundwater analyses underneath industrial installations in which organic solvents are processed, or also when monitoring the groundwater underneath an airport site.

It is possible to operate the device according to the invention "around-the-clock" and it offers a high degree of availability coupled with low maintenance costs. Due to the delimitation of specific components with sum and group parameters, it is possible to measure the impurities, in particular organic solvents, in a very simple manner and yet with precision.

BRIEF DESCRIPTION OF THE DRAWINGS

The invention is described in greater detail in the following with the aid of embodiment examples while reference is made to the drawings. Thus

DETAILED DESCRIPTION OF THE PREFERRED EMBODIMENT

Figure 1:
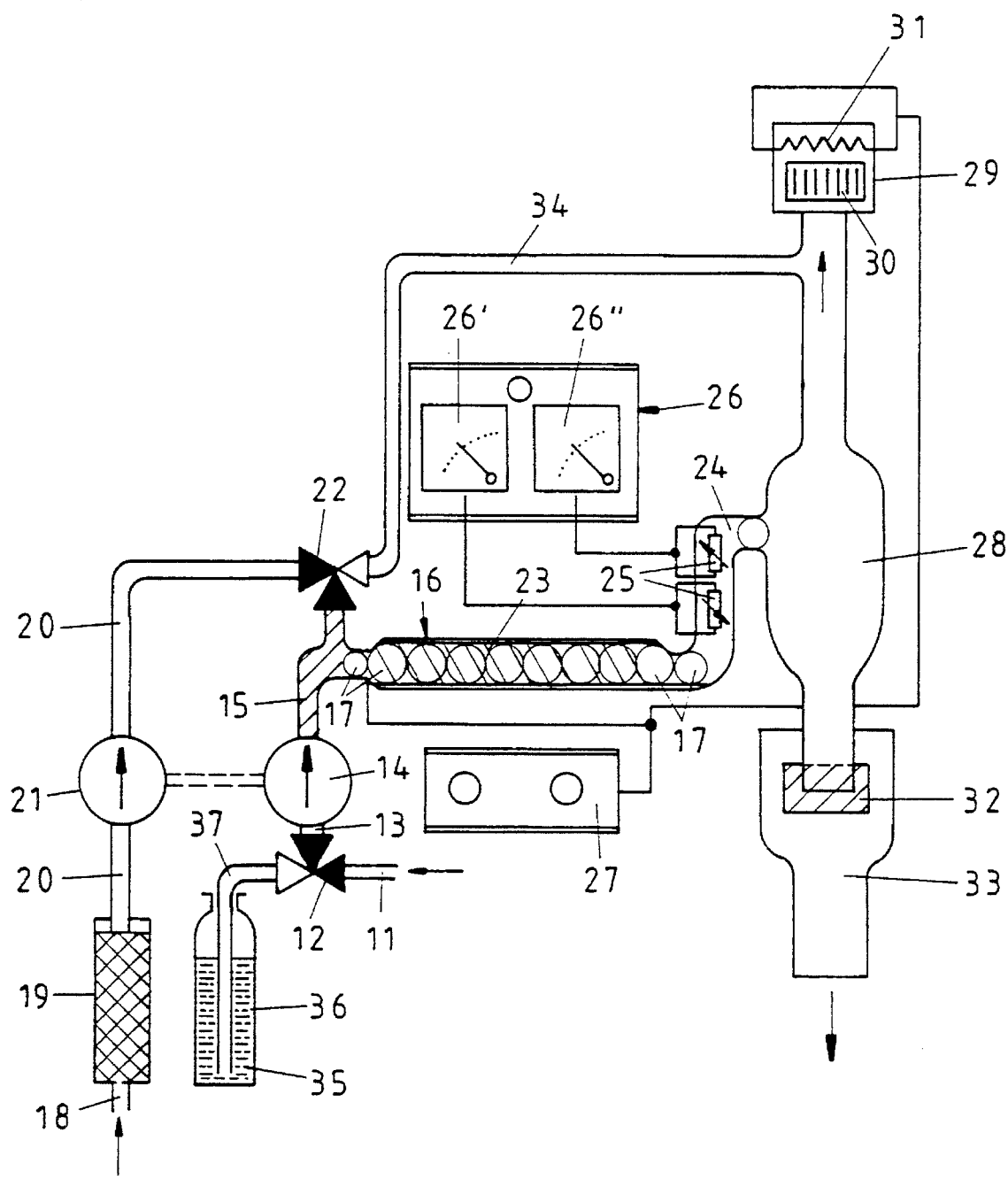
FIG. 1 shows a diagrammatical representation of an embodiment example of the device according to the invention while a measurement operation is in progress.

In the FIG. 1, an embodiment example of the device according to the invention is diagrammatically depicted, to be more precise, in the form of a flow diagram during the impurity measurement. The liquid to be monitored, preferably water, is supplied via a duct 11, in which a valve 12 constructed in the form of a 3-way valve is disposed. When an impurity is being monitored, the valve 12 is, in the manner shown, switched in such a way that it connects the duct 11 to a duct 13 so that the liquid flows into the duct 13.

A pump 14 is mounted inside duct 13 for delivering the liquid, to the outlet side of which a T-shaped duct section 15 adjoins. The horizontal branch of the T-shaped duct section 15 terminates in a mixing chamber 16. The mixing chamber 16 has, by way of example, a length of 100 mm with an internal diameter of 3 mm and an external diameter of 7 mm. Consequently, the volume of the mixing chamber 16 is approximately 0.7 ml. The delivery volume of the pump 14 is designed in such a way that e.g. a liquid rate of flow of 500 ml/h through the mixing chamber 16 is achieved.

In the mixing chamber 16, the liquid is intermixed with carrier gas, which is illustrated by means of the bubbles 17. The carrier gas is produced by air being aspirated via an inlet aperture 18 which terminates in a filter chamber 19 in which activated charcoal is disposed. To the outlet of the filter chamber 19, a duct 20 is fitted, to which a pump 21 for the aspiration and conveying further of the air is connected. The duct 20 terminates in a valve 22 that is constructed in the form of a 3-way valve and which, in the depicted flow diagram, conducts the air from the duct 20 along to the T-shaped duct section 15. The valve 22, just like the valve 12, is constructed in the form of a magnetic valve, i.e. it is electrically controllable.

When impurities are being measured, the pumps 14 and 21 are operated in such a way that the ratio between delivered liquid and delivered carrier gas is constant. In order to achieve this, the pumps 14 and 21 are mechanically coupled so that the ratio of their deliveries remains constant in each case even if changes in the absolute delivery volume do occur. The pumps 14 and 21 serve as dosing units and may also be substituted by other suitable delivery means.

The traces of the measuring gas present in the solution diffuse in the mixing chamber 16, i.e. the traces of the impurities to be measured diffuse into the carrier gas during the residence time of the liquid sample in the mixing chamber 16. By means of the carrier gas bubbles in the mixing chamber which are vortexed due to the flow, this diffusion is very effectively assisted so that the impurities, preferably the dissolved organic solvents, convert into the gas phase to a relatively great extent and intermix with the carrier gas. The liquid is consequently degasified. For adjusting the temperature in the mixing chamber 16, a heating means is provided which will be described in greater detail hereinafter.

Via an intermediate duct piece 24 in which precision resistors 25 are disposed that are connected to an indicating and control means 27, the mixing chamber 16 merges with a separating chamber 28 which serves as phase exchange chamber. The separating chamber 28 brings about a separation of the liquid/gas bubble mixture coming from the mixing chamber 16 into the degasified liquid which is sinking downward and the gas mixture comprising the carrier gas and solvent gas which has converted into the gas phase, which rises upward. The separating chamber 28 extends in the vertical direction and, within the discharge area of the intermediate duct piece 24, is provided with a widened section which is adjoined both upwardly and downwardly by thinner sections. The top section having a reduced cross-section leads to a gas sensor 30 mounted vertically at the top which is preferably disposed in a gas measuring chamber 29. A heating means 31 is provided for adjusting the temperature of the gas sensor 30 and the measuring chamber 29.

The bottom section of the separating chamber 28 having a reduced cross-section terminates in an overflow cap 32 which is disposed in an outlet 33. The overflow cap 32 serves as a flexible closure for draining, degasified liquid so that gas to be measured which diffused from the sample is incapable of escaping. The overflow cap 32 is arranged in such a way that its liquid level lies above the lower outlet aperture of the separating chamber 28.

The gas to be measured (gas mixture) which escaped from the sample solution is measured in the gas measuring chamber 29 which is tempered by the heating means 31. The heating means is constructed in the form of an electrically driven heating coil. The temperature in the gas measuring chamber 29 is thermostatically controlled in such a way that the ambient temperature in the interior of the small measuring chamber lies approximately 3° C. above the temperature of the gas to be measured, i.e. the gas mixture, in order to avoid condensation.

The temperature of the liquid, i.e. the sample solution, is measured with the aid of two resistance thermometers 25 and regulated to the set water temperature of the sample. The pertinent structural elements are to be found in the indicating and control means 26 which is equipped with indicating means 26', 26". With the aid of one of the indicating means it is possible to indicate the target temperature and, by means of the other, the actual temperature of the liquid. The temperature regulation is effected with the aid of the heating means 23 which is constructed in the form of a heating coil in the interior of the mixing chamber 16 and which is supplied with voltage by the voltage supply means 27. The voltage control and/or switching on/switching off of the voltage supply of the heating means 23 is controlled with the aid of control components disposed in the indicating and control means 26 which are not shown, in such a way that the liquid in the mixing chamber acquires the desired temperature. The voltage supply circuit 27 also supplies the heating means 31 with current.

The voltage supply means 27 may be constructed in the form of a controller, with the aid of which the current supply for the heating means 23 and the heating means 31 is maintained constant at a preprogrammed current intensity. The temperatures to be adjusted can be set to values of from 15 through 40° C.

Figure 2:
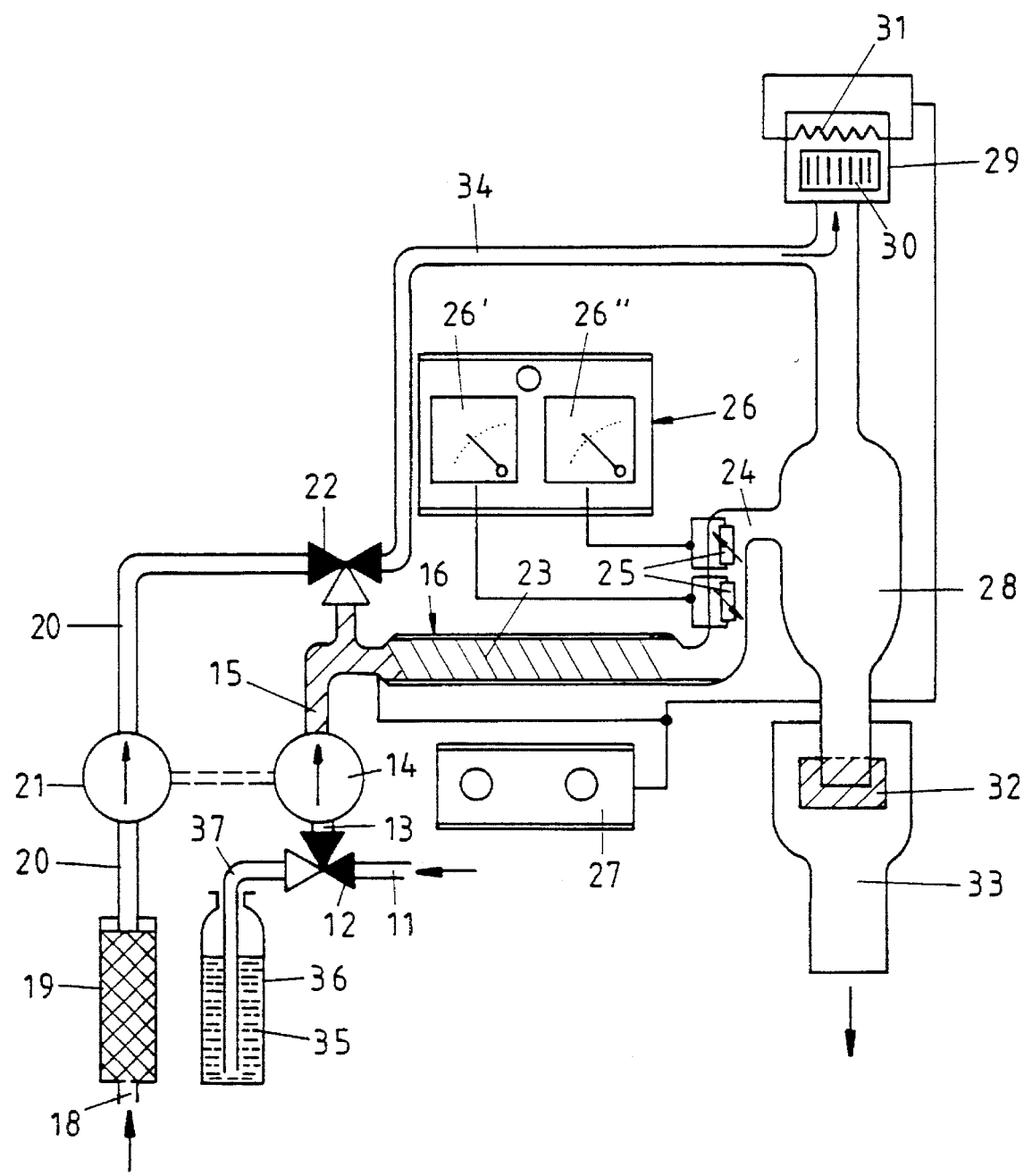
FIG. 2 shows the embodiment example according to FIG. 1 while the zero-point adjustment is being carried out.

In FIG. 2, the embodiment example according to FIG. 1 is shown in the valve position for zero-point adjustment. In order to effect the zero-point adjustment, merely a changing over of the valve 22 is necessary, to be more precise, to passage from the duct 20 to a bypass duct 34 which proceeds from the valve 22 and, while circumventing the mixing chamber 16, terminates in the separating chamber 28 direct, and this preferably within the upper section of the latter immediately before the gas measuring chamber 29. The changeover from normal measurement to zero-point setting is thus possible in an exceedingly simple manner solely by the switchover of a single valve. In the zero-point setting, the sample liquid is piped unchanged via the inlet 11, the valve 12 and the pump 14 to the mixing chamber. However, the carrier gas, i.e. preferably air, does, on account of the switching over of the valve 22, now no longer reach the mixing chamber 16, so that the formation of bubbles as depicted in FIG. 1 no longer takes place. Due to this, only very minimal quantities of gas particles are still able to diffuse from the mixing chamber 16. Consequently, the impurity concentration in the separating chamber 28 is greatly reduced. The carrier gas, i.e. the solvent-free air purified by means of the activated charcoal filter, now arrives via the bypass duct 34 in the separating chamber 28 direct and the gas measuring chamber 29. There it displaces possibly still present gas particles coming from the sensor housing through the separating chamber 28 into the outlet 33. The gas sensor 30 is therefore exposed exclusively to zero gas, i.e. zero-point air, so that the signal emitted by the same forms the zero-point signal. Hereby a reliable zero adjustment can be brought about.

In order not to merely be able to set the zero point but to also be able to calibrate the course of the calibration curves, by preference subsequent to the setting of the zero point in the valve position as per FIG. 2, a changeover from the normal sample solution to the standard solution 35 is effected. The standard solution 35 is in a receptacle 36 which, via a duct 37, communicates with the valve 12. For the calibration, the valve 12 is switched in such a way that the duct 37 is switched with the duct 13 to passage, while the valve 22 is once more switched back into the position as per FIG. 1. Consequently, in this position, by means of the pumps (dosing units) 14 and 21, both the standard solution as well as also the carrier gas are piped into the mixing chamber 16. The mode of operation in this case is the same as when the normal sample liquid is measured since bubbles are once again formed in the mixing chamber 16. In this case, the dissolved gases comprised in the standard solution, which is adjusted to a defined value of concentration, diffuse into the carrier gas and reach the separating chamber 28 in the upward direction. Accordingly, in the gas sensor 30, a corresponding gas concentration prevails which is electronically evaluated. Since the gas concentration has a defined value owing to the employed standard solution, the same may be used for the calibration of the measured values.

Figure 3:
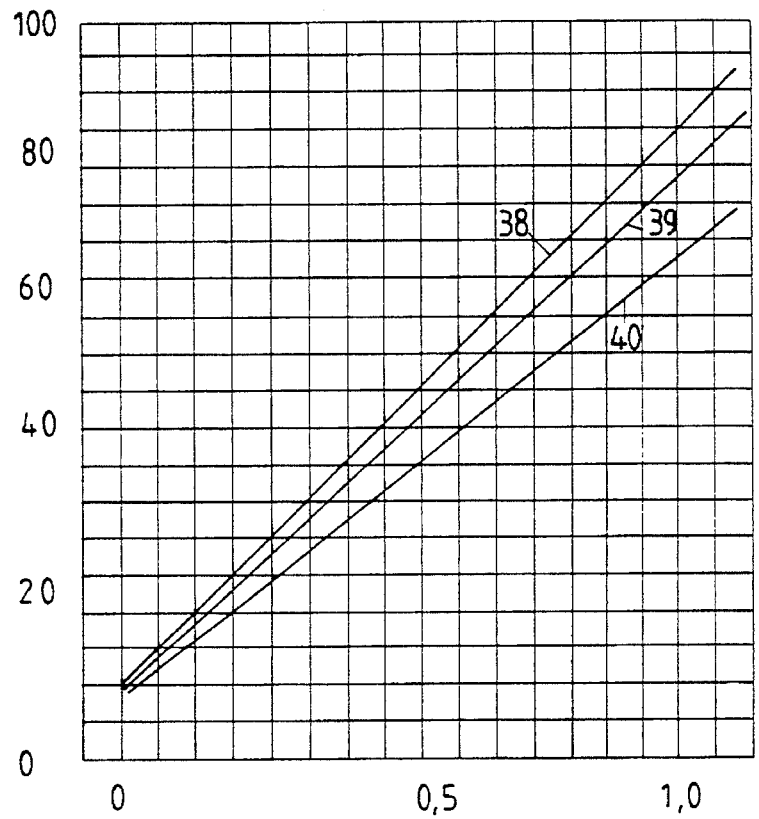
FIG. 3 shows several calibration curves.

In FIG. 3, the calibration curves of three different substances are shown. On the abcissa, the concentration is traced in ppm, while the ordinate reproduces the scale divisions. The curve 38 represents the calibration curve for carbon tetrachloride, while the curves 39 and 40 illustrate the calibration curves of 1.2 dichloroethane (curve 39) and methylene chloride (curve 40). Already at exceedingly low concentration values of below 1.0 ppm, a clear scale deflection is evidently already obtained so that a highly precise measurement and detection of even the minutest impurities is possible.

Figure 4:
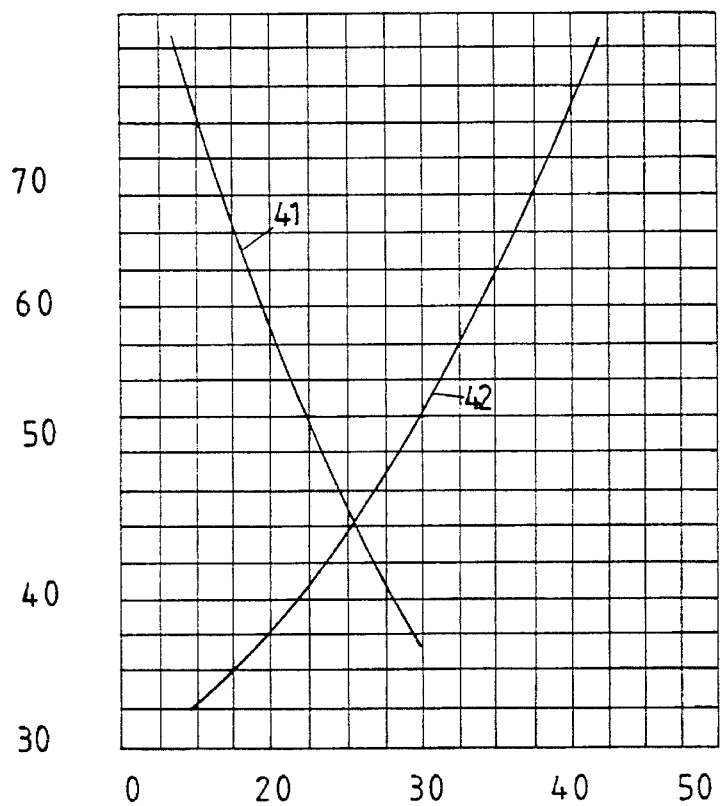
FIG. 4 shows temperature and resistance characteristic curves.

In FIG. 4, the curve 41 illustrates the course of the temperature (in °C), the scale deflection, i.e. the scale divisions, are traced on the ordinate. Obviously, the scale deflection is significantly affected at a certain concentration by the temperature. The regulation of the temperature thus renders possible a precise measurement, in which each measured value can be allocated direct to a specific concentration.

The curve 42 in FIG. 4 shows the course of the resistor $R_i$.

Figure 5:
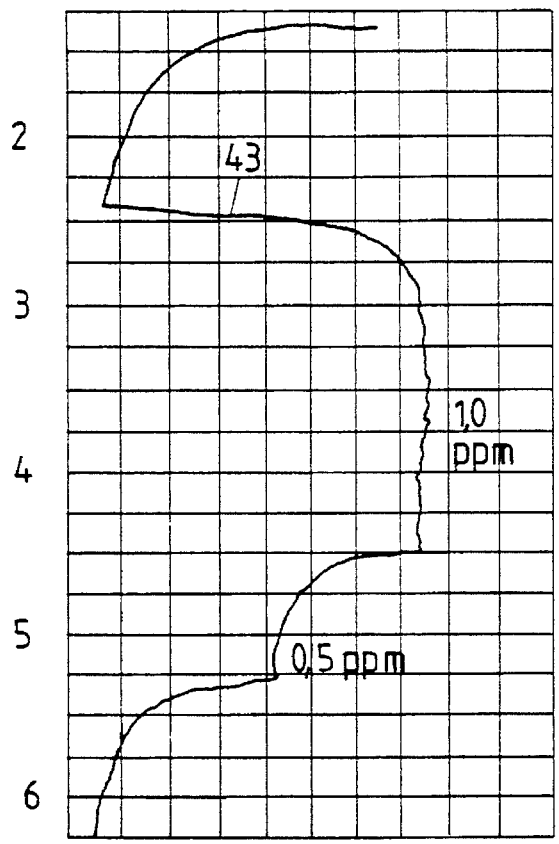
FIG. 5 shows a measurement record during the measurement of methylene chloride.

In the FIG. 5, a measurement result obtained when measuring methylene chloride is depicted in the form of a registration strip.

The achieved calibration curve is identified with 43. The concentration of methylene chloride was in each case changed between the values of 0, 0.5 ppm and 1 ppm. In FIG. 5, the time axis proceeds downwardly. In the concentration of 1 ppm methylene chloride, a deflection of 75 scale divisions was obtained, while the zero point (at concentration 0) lies at 7 scale divisions. The 90% deflection was reached at 68.6 scale divisions so that the difference was between 100% and 90% at 6.5 scale divisions. The increase time from 0 to 90% amounted to 7 minutes.

In the concentration of 0.5 ppm, a deflection of 42 scale divisions was obtained at a zero point of 7 scale divisions. The 90% deflection was reached at 36.5 scale divisions in 5 minutes. From the course of the curve 43 it becomes apparent that the measuring apparatus responds very rapidly to changes in the concentration and also reaches the final value within a relatively short period of time.

Figure 6:
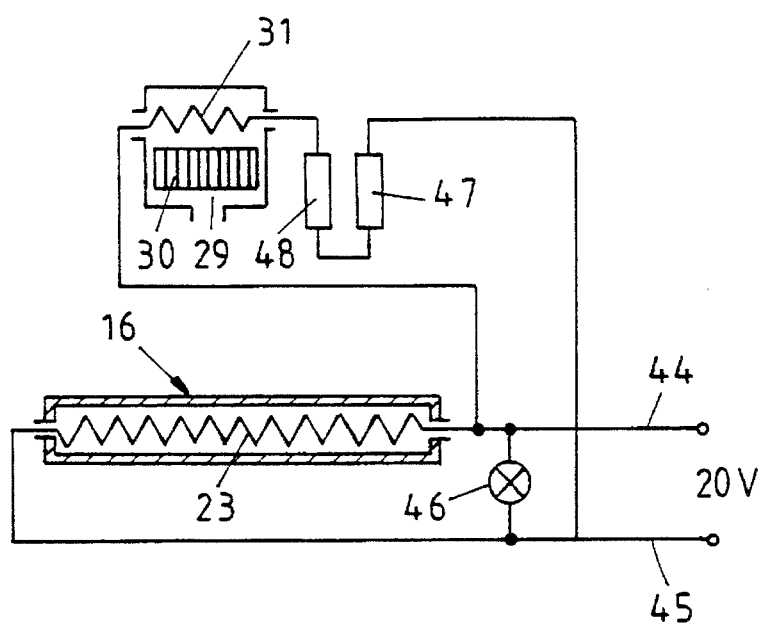
FIG. 6 shows a circuit diagram of the temperature control of the mixing chamber and of the gas sensor.

In FIG. 6, the heating means 23 and 31 as well as the associated wiring are illustrated in greater detail. The heating means 23 lies directly in the sample flow path through the mixing chamber 16, while the resistance of the heating coils is 30 Ohm. A voltage of 20 V is applied to the electric heating means 23 via lines 44, 45 so that a heating current of 0.66 A results. Consequently, the heating power is 13.3 V. It is possible to indicate with the aid of an indicating means 46, preferably in the form of an indicator lamp which is inserted between the lines 44 and 45, whether the heating is switched on or off. The indicator lamp lights up each time the heating means 23 is switched on, i.e. when the input voltage is applied.

Between the lines 44, 45, i.e. located parallelly to the heating means 23, a series connection comprising the heating means 31 andseries resistors 47,48 is inserted. The heating means for the gas sensor housing has a total resistance value of 100 Ohm, of which 72 Ohm account for the two series resistors 47, 48 Each series resistor 47, 48 has a respective resistance value of 36 Ohm. The resistance value of the heating coils therefor lies at just under 30 Ohm. By means of these series resistors 47, 48, the current passing through the heating means 31 is reduced, compared with the current flow through the heating means 23. On account of the input voltage of 20 V, a current flow of 0.2 A results, so that the power drain is 4 Watt.

Figure 7:
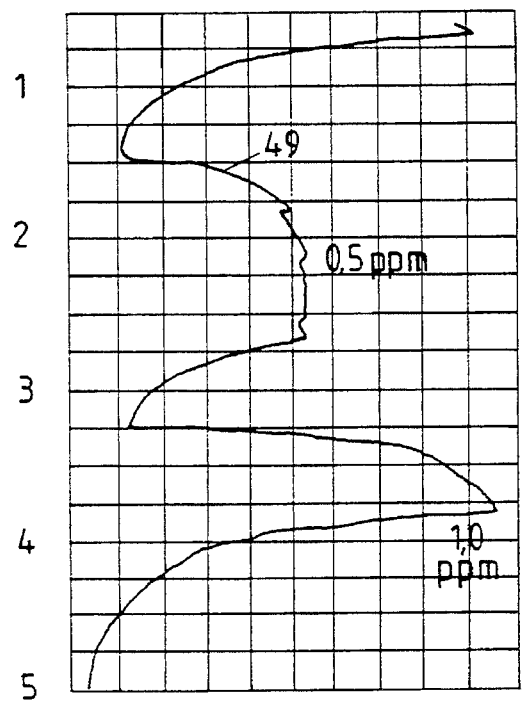
FIGS. 7 and 8 show further measurement curves.

In FIG. 7, the course of the calibration curve when measuring carbon tetrachloride is traced with variations of the concentration value of between 0, 0.5 and 1 ppm. The calibration curve is identified with 49. In this case, the time axis proceeds downwardly, as in FIG. 5. For the 90% time, the following values resulted: At a concentration of 1 ppm, the full deflection at 100% was at 95 scale divisions and, at 90%, at 85.5 scale divisions so that the 90% difference from the zero point amounted to 85.5 scale divisions. The 90% time in this case was 15 minutes.

With a concentration of 0.5 ppm, the full deflection at 100% comprised 53 scale divisions so that the 90% value corresponded to a difference of approximately 48 scale divisions from the zero point. The zero point lay at 6 scale divisions. In this case the 90% time was 3 minutes.

Figure 8:
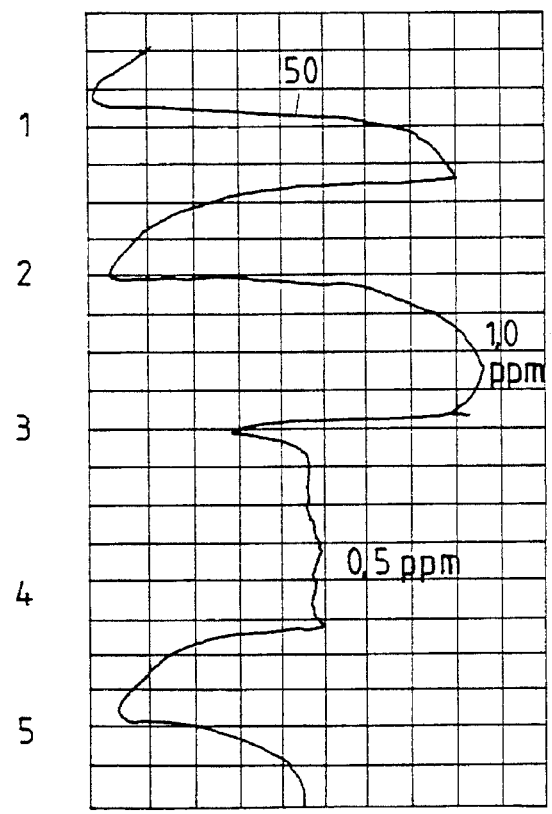

In FIG. 8, a calibration curve 50 similar to the curves shown in the FIGS. 5 and 7 for 1.2 dichloroethane has been traced, while the concentration was changed between 0. 0.5 and 1 ppm. In this case the following resulted for the 90% time:

With a concentration of 1 ppm, with a 100% deflection, a deflection of 88 scale divisions was achieved. The 90% time had thus elapsed when approximately 80 scale divisions were reached, in which case, for the indication change from 3 (with zero concentration) through 80 scale divisions, a space of time of minutes was required. This corresponded to the 90% time.

With a concentration of 0.5 ppm, a full deflection of approximately 50 scale divisions resulted. The time for reaching a 90% deflection, i.e. from 45 scale divisions, was 7 minutes at a zero-point value of 3 scale divisions.

Consequently, the invention permits a very expeditious, precise and effective measurement of even the smallest impurities. In this case, the device is made up of three separate units, viz. the analyzer shown in the FIGS. 1 and 2, the current supply means with temperature regulation of the analyzer, as shown partly in FIG. 6, and ultimately the evaluating part with registration means. The latter brings about the detection and evaluation of the concentration-dependent parameter change of the gas sensor as e.g. the change in conductivity. Since this evaluation method is known, it is not dealt with in greater detail here.

Figure 9:
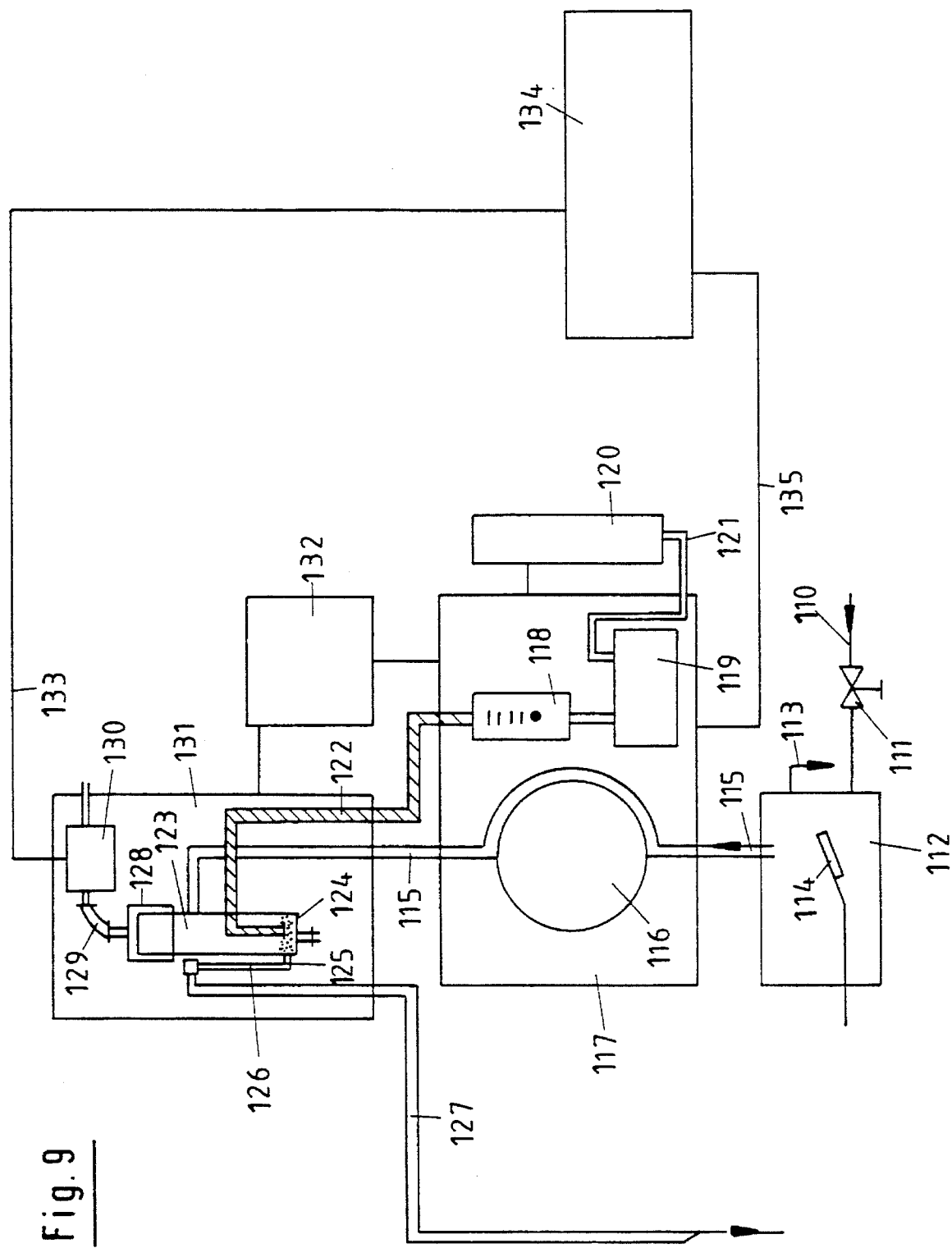
FIG. 9 shows a diagrammatical representation of an embodiment example of the device according to the invention.

In the embodiment example shown in FIG. 9, the liquid to be measured, more particularly water, with impurities in the form of organic solvents or other components, is introduced via a supply line 110 with shut-off or butterfly valve 111 into an overflow receptacle 112. The overflow receptacle 112 is, within its top area, provided with an overflow 113 so that, when the supply of liquid is adequate, a liquid level automatically comes about in the overflow receptacle 112 which extends as far as to the overflow 113.

In the overflow receptacle 112, a level detector in the form of a float switch 114 is provided. If the supply of liquid in the overflow receptacle 113 is too low, the float switch closes and emits a signal so that a defect message is produced when the liquid is inadequate.

By preference, the liquid is conducted continuously to the overflow receptacle 112 so that a continuous monitoring is achieved. But it is also possible to merely introduce liquid by charges into the overflow receptacle, by way of example, in order to carry out random measurements.

From the overflow receptacle 112, the liquid to be measured is drawn off via a line 115 which interacts with a dosing unit in the form of a pump 116. With the aid of this pump 116 it is possible to determine and control the quantity of liquid delivered via the line 115. The pump 116 is preferably constructed in the form of a hose pump, but may also be of a different construction.

The pump 116 and a section of the line 115 is accommodated in a housing 117 which also encloses delivery components for the carrier gas, viz. a regulating valve 118 with a flow indicator and a dosing unit in the form of a pump 119, preferably a diaphragm pump. Any suitable gas may be employed as carrier gas. Preferably, however, owing to the universal availability and simplicity, air is used as carrier gas, said air being aspirated via a filter 120, by preference an activated charcoal filter and, via a duct 121 introduced into the pump 119.

The volume of the quantity of liquid removed in a defined manner from the overflow receptacle 112 is at a fixed ratio to the carrier gas dosage, i.e. to the volume of carrier gas or air delivered through the pump 119 and the control valve 118. The liquid delivered through the pump 116 is introduced into a reaction chamber 123 via the line 115. The reaction chamber 123 is preferably constructed in the form of a vertically arranged container which may be cylindrical and have a uniform diameter. The line 115 terminates within the top half of the reaction chamber 123.

The carrier gas delivered through the pump 119 via the regulating valve 118, by preference air, is likewise introduced via a duct 122 into the reaction chamber. The point where the carrier gas is charged into the reaction chamber 123 is located far below the point of entry of the line 115, to be more precise, preferably in the immediate vicinity of the bottom of the reaction chamber 123.

Fine-pored frit 124 is to be found within the bottom area of the reaction chamber 123. The carrier gas and the liquid come into contact with the fine-pored frit, as a result of which the impurities dissolved in the liquid, such as e.g. organic solvents, are converted into the gas phase and, together with the carrier gas bubbles, rise upwardly in the reaction chamber 123 through the liquid. The carrier gas is supplied in such a way that it acts within the frit area direct, for which purpose the charging point for the carrier gas is preferably located immediately within the area of the frit 124. For this, the line 122 may be introduced into the interior of the reaction chamber 123 as far as to almost reach the bottom of the latter.

Via an outlet 125, the liquid flows out of the reaction chamber 123. The point of exit of the outlet 125 from the reaction chamber 123 is located within the bottom area so that solely liquid is drained off which has permeated the frit and has been degasified in the process. The outlet 125 communicates with a curved section 126 which proceeds upwardly to begin with and, while describing a sharp U-shaped lateral bend, merges with an outlet pipe 127, via which the liquid is drained off. The apex of the curved section 126, i.e. of the elbow, lies below the roof area of the reaction chamber 123, but within its top half, preferably at the level of the discharge point of the line 115 into the reaction chamber. Consequently, in the reaction chamber 123, a permanent liquid level appears which reaches as far as to the top point of the elbow 126.

When necessary, in order to render possible an evacuation of the reaction chamber, the same may be provided on the underside with an outlet which can be shut, via which the liquid and/or the frit 124 can be drained off from the reaction chamber 123.

Within the upper area of the reaction chamber 123 which serves as a stripper container, a cap 128 is mounted which prevents an escape into the environment of the gas mixture composed of the carrier gas and the impurities gas. A measuring line 129 discharges above the cap 128 which is provided with an integrated pipeline heating means for regulating the measuring line 129 to a constant temperature. The measuring line 129 conducts the gas mixture to be measured to a gas sensor 130 which is preferably constructed in the form of a semiconductor gas sensor. The gas sensor 130 measures the impurity components comprised in the gas to be measured, by preference on a physical basis.

The reactor chamber 123 with cap 128 and measuring line 129 as well as the gas sensor 30 are accommodated inside a housing which is provided with an outlet proceeding from the gas sensor 130 for the outflow of the measured gas. In order to maintain the vapor pressure of the sample liquid with the impurities, such as e.g. the organic solvents, constant, the housing with the reaction chamber 123 as well as the incorporated pipeline heating means for the measuring line 129 are maintained at a constant temperature. The temperature regulation is brought about by a controller 132. It is possible for the controller 132 to additionally regulate also the temperature of the housing 117, so that carrier gas and liquid, already when entering ring into the housing 131, are adjusted in their temperature to suitable values, preferably to the temperature value of the housing 131. The liquid which has already been roughly filtered in advance possesses, preferably within the inlet area, a temperature of 20° C. In order to also permit an operation at higher temperatures of the liquid to be carried out, a cooling means may be additionally provided which cools the liquid to e.g. 20° C. The cooling means may be mounted within the area of the inlet 110 or also between the overflow receptacle 112 and the pump 116.

The gas sensor 130 is disposed in an integrated housing which serves as a small gas measurement chamber and is provided with a separate thermostat. The temperature of the gas sensor and of the gas measurement chamber is preferably regulated in such a way that it lies very little above the gas temperature, e.g. 3° C. above it. Hereby a condensation of the gas to be measured within the area of the gas sensor 130 is avoided.

The gas sensor 130 is, via an electric line 133, connected to an evaluation unit 134 which brings about the electric supply of the gas sensor 130, when this is necessary, and evaluates the output signal generated by the latter which changes in dependence of changes in the concentration. The evaluating unit 134 is further connected via an electric line 135 to the housing 117 and the components disposed therein in order to supply said components with voltage and/or for conveying information regarding the operating parameters such as e.g. the actual delivery volume, the temperature or the like to the evaluating unit 134.

Prior to the device being put into operation and also later at fixed intervals, zero point and standard value are checked and corrected. This may be done in the manner described in the DE 22 60 088 C2. For setting the zero point, air is caused to flow around the gas sensor 130, while, during the calibration, i.e. the setting of the standard value, a comparison solution is introduced via the line 115 into the reaction chamber 123, while carrier gas is supplied at the same time.

The electronic evaluating means 134 may be equipped with two limiting value contacts, of which the first responds when low concentrations are exceeded and triggers an alarm. The second, more highly set limiting value contact, sets off a system of samplings, with which it is possible to immediately or later, selectively and quantitatively evaluate the individual measurement components. The sensitivity of the measurement range is consequently, with the aid of these limiting value contacts, set in such a way that, with average values of the water balance of organic solvents, no alarm is set off. The setting-off of the alarm consequently implies that an impurity above the normal water composition is present, as may occur when organic toxic substances, such as e.g. perchloroethylene, trichloroethylene, methylene chloride or decomposition products of the chemical industry are introduced.

So long as the second limiting value contact has not been reached, i.e. the concentration lies below this value, the impurities, particularly the organic solvents, are summarily and quantitatively measured. At an increased measured value, a selective measurement of one or several individual components can be controlled in a simple fashion with the aid of a gas chromatograph, and this for the duration of the increased measured value.

With the aid of a further limiting value ontact it is possible to introduce the continuous liquid sample into a system of samplings in order to subject them to a test once more at a later date.

The combined and simplified measurement method used in the invention offers substantial economic and service-compatible vantages since, due to the continuous mode of operation, a putting on the alert in time of the operating staff as well as an exact definition of the impurity component(s) is possible. The delimitation of specific components by sum or by group parameters for the continuous measurement, given the multitude of organic impurities occurring in water, represents a useful solution and offers the advantage of a rapid measured value detection which is of special importance because accidents may often take place having only a short duration but involving relatively high concentrations. Such accidents are detectable only with difficulty when employing continuously operating equipment. Impurities of this kind represent a special hazard especially in the preparation of drinking water since the removed raw water often comprises a mixture bank-filtered water and groundwater. Just like the river water monitoring, also the measurement of effluents from communal and industrial sewage treatment plants calls for a continuous monitoring. If, on this occasion, the moment and the concentration of the pollution, as well as the differentiation of the individual impurities is of interest, these items of information may be acquired by a selective measurement triggered by the device according to the invention, so as to enable one to take appropriate countermeasures for the elimination of the impurity elements as quickly as possible. It is also possible to employ the device for the monitoring of the groundwater, e.g. in the event of industrial accidents and leakages of fuel tanks or containers holding organic solvents. It is possible to hereby localize or contain the proliferation of the impurity in the groundwater. Moreover, a continuous monitoring of the groundwater underneath refuse disposal sites is possible so as to enable one to be continuously informed of the state of the leachate (percolating water) and the groundwater. A further area of operation is the monitoring of the effluent from activated charcoal filter plants in which the condensate running off from the water separator of the filter plant, whose limiting values lie within the lower ppm range, have to be monitored for solvent traces before being introduced into the settling tank.

The invention thus provides a device which operates with modest technical resources and a high degree of availability at low costs and is capable of documentarily recording the measured values. In this connection it is possible to detect even very low concentrations within the lower ppm and ppb range, but it is likewise possible to detect also higher concentrations. At the same time, with the invention, a simplified measurement method is also provided which operates with phase exchange and which can be performed continuously, in which the gaseous impurities dissolved in the liquid, more particularly water, are converted into the gas phase and are quantitatively evaluated with the aid of a gas sensor.

Figure 10:
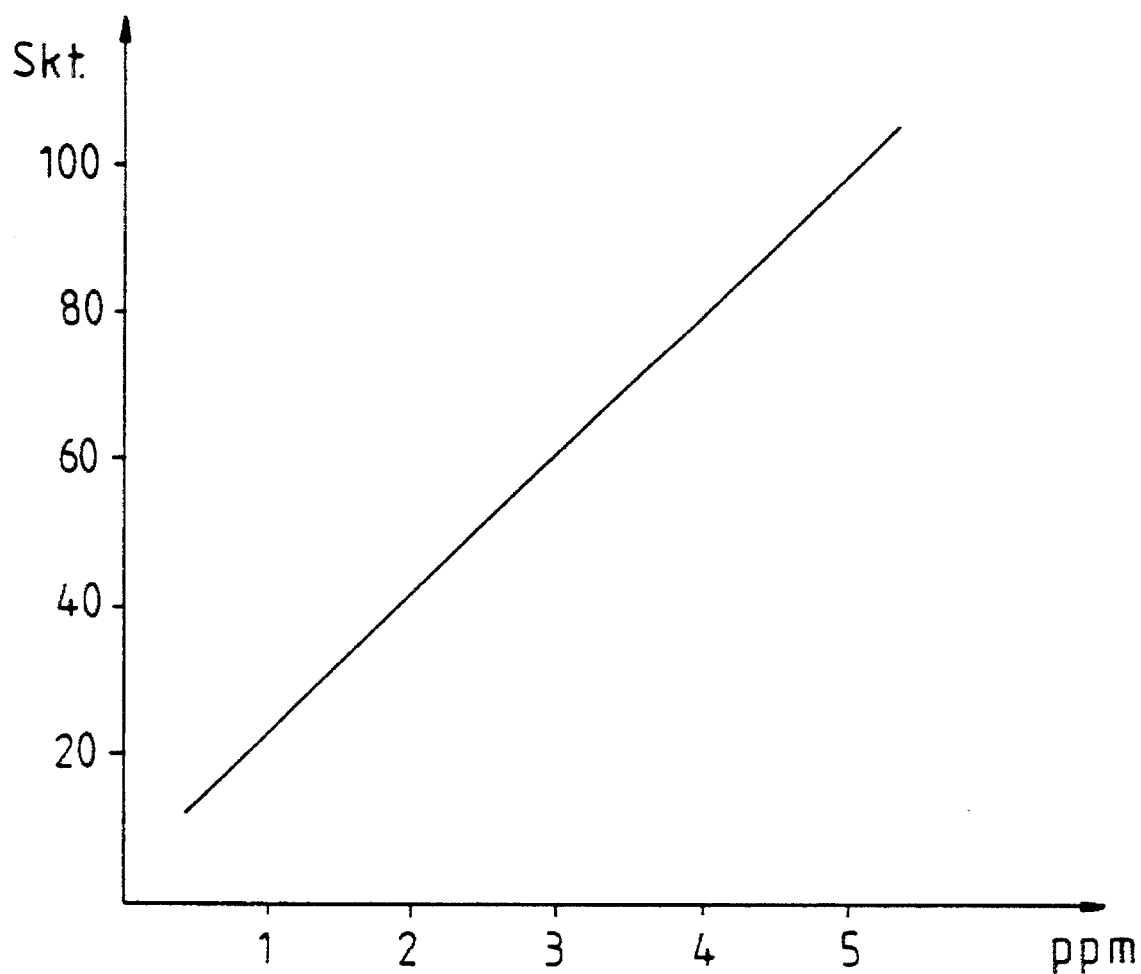
FIG. 10 shows a calibration curve.

The accuracy of the measurement which can be carried out with the invention is illustrated by the curve shown in FIG. 10, which depicts the calibration curve of trichloroethane. Evidently, already extremely low concentration proportions of trichloroethane of below 1 ppm lead to a distinct deflection on the measuring scale. On the abcissa, the concentration is traced, while the ordinate represents the scale divisions, i.e. the respective measurement deflection. It is true that the invention is designed preferably for continuous long-term monitoring of liquids for impurities, a discontinuous operation is also possible, of course, depending on the range of application, likewise a monitoring of the concentration of desired substances, provided that it is possible to convert the same by means of carrier gas from the liquid into the gas phase.

What is claimed is:

1. An apparatus for measuring organic solvent impurities in a liquid, said apparatus comprising:

a mixing chamber defined by a horizontally extending elongate pipe and provided with heating means for maintaining temperature in the mixing chamber substantially constant;

means for delivering the liquid into the mixing chamber, said liquid delivering means comprising a liquid conduit and metering means arranged in said liquid conduit for delivering a predetermined amount of the liquid into said mixing chamber;

means for delivering a carrier gas, which is substantially free from organic solvents, into the mixing chamber;

wherein the organic-free carrier gas intermixes with the liquid and causes conversion of at least a part of the impurities, which are contained in the liquid, into a gas phase, whereby a gas mixture, which contains the organic solvent-free carrier gas and impurities converted into the gas phase, is produced, said carrier gas delivering means comprising a carrier gas conduit and metering means arranged in said carrier gas conduit for delivering a predetermined amount of the carrier gas into said mixing chamber, said metering means of said liquid delivering means and said metering means of said carrier gas delivering means operating synchronously with each other for delivering the carrier gas and the liquid into the mixing chamber at a predetermined ratio therebetween;

a separating chamber into which the liquid and the gas mixture flows from the mixing chamber and in which the liquid is separated from the gas mixture;

a temperature detector for detecting a temperature leaving the mixing chamber;

a gas sensor located in an upper portion of said separating chamber for measuring the impurities contained in the gas mixture, said gas sensor being provided with heating means; and means for calibrating said gas sensor, said calibrating means comprising a gas switch-over valve located upstream of said carrier gas metering means in said gas conduit, a gas by-pass conduit for communicating said gas switch-over valve with the upper portion of said separating chamber, and liquid switch-over valve located in said liquid conduit and connected witch a conduit communicating with a source a standard solution.

2. An apparatus as claimed in claim 1, further comprising an activated charcoal filter located upstream of the carrier gas metering means.

3. An apparatus as claimed in claim 1, wherein the liquid metering means and the carrier gas metering means are mechanically connected with each other and comprise each a pump.

4. An apparatus as claimed in claim 1, wherein the separating chamber has a liquid outlet in a bottom portion thereof, and a cap for covering the outlet.

* * * * *